(12) United States Patent
Tybinkowski et al.

(10) Patent No.: US 7,072,434 B1
(45) Date of Patent: Jul. 4, 2006

(54) CARRY-ON BAGGAGE TOMOGRAPHY SCANNING SYSTEM

(75) Inventors: Andrew P. Tybinkowski, Boxford, MA (US); Ronald Swain, Reading, MA (US); Robert Williams, Wilmington, MA (US); Nicholas Svencer, Cambridge, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 10/757,754

(22) Filed: Jan. 15, 2004

Related U.S. Application Data (60) Provisional application No. 60/440,488, filed on Jan. 16, 2003.

(51) Int. Cl.
*G01N 23/00* (2006.01)

(52) U.S. Cl. .............................. 378/4; 378/57; 378/203

(58) Field of Classification Search ................ 378/4, 378/57, 203, 20, 193, 195, 196, 197
See application file for complete search history.

(56) References Cited

U.S. PATENT DOCUMENTS

| | | | |
|---|---|---|---|
| 4,239,969 A * | 12/1980 | Haas et al. ................... 378/57 |
| 5,661,774 A | 8/1997 | Gordon et al. .............. 378/101 |
| 5,796,802 A | 8/1998 | Gordon ........................... 378/8 |
| 5,818,897 A | 10/1998 | Gordon ......................... 378/19 |
| 5,937,028 A * | 8/1999 | Tybinkowski et al. ....... 378/203 |
| 5,982,844 A * | 11/1999 | Tybinkowski et al. ......... 378/4 |
| 6,185,272 B1 | 2/2001 | Hiraoglu et al. .............. 378/57 |
| 6,188,743 B1 | 2/2001 | Tybinkowski et al. ......... 378/4 |
| 6,188,745 B1 | 2/2001 | Gordon ......................... 378/19 |
| 6,256,404 B1 | 7/2001 | Gordon et al. .............. 382/131 |
| 6,317,509 B1 | 11/2001 | Simanovsky et al. ....... 382/131 |
| 6,418,189 B1 | 7/2002 | Schafer ........................ 378/57 |

* cited by examiner

*Primary Examiner*—Edward J. Glick
*Assistant Examiner*—Courtney Thomas
(74) *Attorney, Agent, or Firm*—McDermott Will & Emery LLP (57) ABSTRACT

A tomography scanner system including a gantry having an outer, non-rotating support ring, and an inner rotatable component ring supported for rotation within the support ring about a rotation axis of the gantry. An x-ray source and an x-ray detector array are secured to the rotatable component ring for rotation with the component ring, and an x-ray containment shield encloses the x-ray source and the x-ray detector array and is secured to the rotatable component ring for rotation with the component ring.

21 Claims, 6 Drawing Sheets

CARRY-ON BAGGAGE TOMOGRAPHY SCANNING SYSTEM

CROSS-REFERENCE TO RELATED APPLICATION

The present application claims priority from U.S. Provisional Patent Application Ser. No. 60/440,488 filed on Jan. 16, 2003, which is assigned to the assignee of the present application and incorporated herein by reference.

FIELD OF THE INVENTION

The present disclosure relates generally to x-ray scanning systems and, more particularly, to an x-ray baggage scanning system. Even more particularly, the present disclosure relates to an x-ray computed tomography scanning system adapted to scan luggage for detection of explosives, drugs, and other contraband.

BACKGROUND OF THE DISCLOSURE

The Federal Aviation Administration (FAA) and other similar agencies throughout the world have the daunting task of identifying dangerous devices and/or contraband within passenger baggage and within a time-frame that will not generally impede passenger travel time. Many x-ray baggage scanning systems in use today are of the "line scanner" type and include a stationary x-ray source, a stationary linear detector array, and a conveyor belt for transporting baggage between the source and detector array as the baggage passes through the scanner. The x-ray source generates a stationary x-ray beam that passes through and is partially attenuated by the baggage, as the baggage is moved into and positioned within the beam, before being received by the detector array. During each measuring interval, each detector of the detector array generates data representative of the integral of the density of the planar segment of the baggage through which the detected portion of the x-ray beam passes. The data acquired by the detector array during each measuring interval is used to form one or more raster lines of a two dimensional image. As the conveyor belt transports the baggage past the stationary source and detector array, the scanner generates a two dimensional image representative of the density of the baggage, as viewed by the stationary detector array. The density image is typically displayed for analysis by a human operator.

It has been suggested to use x-ray computed tomography (CT) as a part of a baggage scanner to identify objects within baggage positioned in the scanner. At least one of these designs, described in U.S. Pat. No. 5,182,764 (Peschmann et al.) and U.S. Pat. No. 5,367,552 (Peschmann et al.) (hereinafter the '764 and '552 patents), for example, has been commercially developed and are referred hereinafter as the "In Vision Machine". The In Vision Machine includes a CT scanner of the third generation type. Third generation type CT scanners are particularly useful in the medical arts and are often used for imaging sections of the human body. Third generation scanners typically include an x-ray source and an x-ray detector system secured respectively to diametrically opposite sides of an annular-shaped gantry platform or disk. The gantry disk is rotatably mounted within a gantry support so that in operation the disk continuously rotates about a rotation axis while x-rays pass from the source through an object positioned within the opening of the disk to the detector system. During a scanning procedure, baggage passes along the rotation axis through the rotating gantry disk.

The EXACT™ AN6000, which is available from International Security Systems Corporation (www.analogic.com/ISS), which is a subsidiary of the assignee of the present disclosure, Analogic Corporation, is an advanced CT system for the detection of explosives, drugs, and other contraband in carry-on baggage. The EXACT™ AN6000 generates 3-D image data of all objects in a bag, gathers all data in one pass, allows automatic analysis of entire contents of bag, and can handle up to 600 bags per hour. Analogic's EXACT™ AN6000 is a dual energy, helical-cone-beam, multi-slice CT system that provides a complete set of CT images of an entire three-dimensional object as it passes along the baggage conveyor. The system includes a high efficiency, wide dynamic range, solid-state x-ray detector array consisting of 6048 detectors. Rotating at 90 RPM, this system takes up to 720 sets of 6048 measurements per rotation every two-thirds of a second. The system presents both projection and axial images of this moving object for analysis by the operator. The EXACT™ AN6000 CT system is covered by at least the following U.S. patents which are owned by Analogic Corporation: U.S. Pat. Nos. 5,661,774; 5,796,802; 5,818,897; 5,937,028; 6,185,272; 6,188,745; 6,256,404; 6,317,509 and 6,418,189.

The EXACT™ AN6000 is the heart of the eXaminer 3DX™ 6000 Explosive Detection System (EDS), the first single-unit, second-generation CT system certified by the U.S. Federal Aviation Administration and developed in cooperation with L-3 Communications. The EXACT™ AN6000 is also the system of choice for detection of drugs and other contraband. Equipped by ISS with our own workstation and custom drug algorithms, the EXACT™ AN6000 has been successfully demonstrated to the U.S. Customs Service, detecting small quantities of contraband. Sophisticated software automatically isolates bag contents unambiguously and analyzes them, evaluating them against the known characteristics of explosives or narcotics. If a match is found, the system alerts the operator, highlights the area of concern for further analysis, and provides a full rotating 3-D image of the potential threat.

What is still desired is a an improved system for detecting explosives, drugs, and other contraband in a typical piece of carry-on baggage. Preferably, the system will be an x-ray computed tomography scanning system adapted to scan carry-on baggage for detection of explosives, drugs, and other contraband.

SUMMARY OF THE DISCLOSURE

The present disclosure provides a new and improved x-ray computed tomography scanning system adapted to scan carry-on baggage for detection of explosives, drugs, and other contraband. Among other features and benefits, the system include an improved conveyor system, an improved rotating x-ray shielding structure, and an improved gantry structure.

One exemplary embodiment of a tomography scanner system constructed in accordance with the present disclosure includes a gantry having an outer, non-rotating support ring, and an inner rotatable component ring supported for rotation within the support ring about a rotation axis of the gantry. An x-ray source and an x-ray detector array are secured to the rotatable component ring for rotation with the component ring, and an x-ray containment shield encloses the x-ray source and the x-ray detector array and is secured to the rotatable component ring for rotation with the component ring.

According to one aspect of the present disclosure, the component ring includes a mounting face extending perpendicular to the rotation axis and the x-ray source, the x-ray detector array and the x-ray containment shield are secured to the mounting face of the component ring.

According to another aspect, the system further includes a first, non-rotating x-ray containment tunnel extending from an open end to the rotating x-ray containment shield, coaxial with the rotation axis of the gantry, and a second, non-rotating x-ray containment tunnel extending from the rotating x-ray containment shield to an open end, coaxial with the rotation axis of the gantry.

According to an additional aspect, the system further includes a conveyor system extending within the tunnels and through the gantry between the open ends of the tunnels so that a piece of baggage placed on the conveyor system at one of the open ends will be carried through the gantry to the other of the open ends.

Other features and advantages of the presently disclosed disclosure will become apparent by reference to the following description taken in connection with the accompanying drawings.

BRIEF DESCRIPTION OF THE DRAWINGS

Like reference characters designate identical or corresponding components and units throughout the several views.

DETAILED DESCRIPTION OF EXEMPLARY EMBODIMENTS

Figure 1:
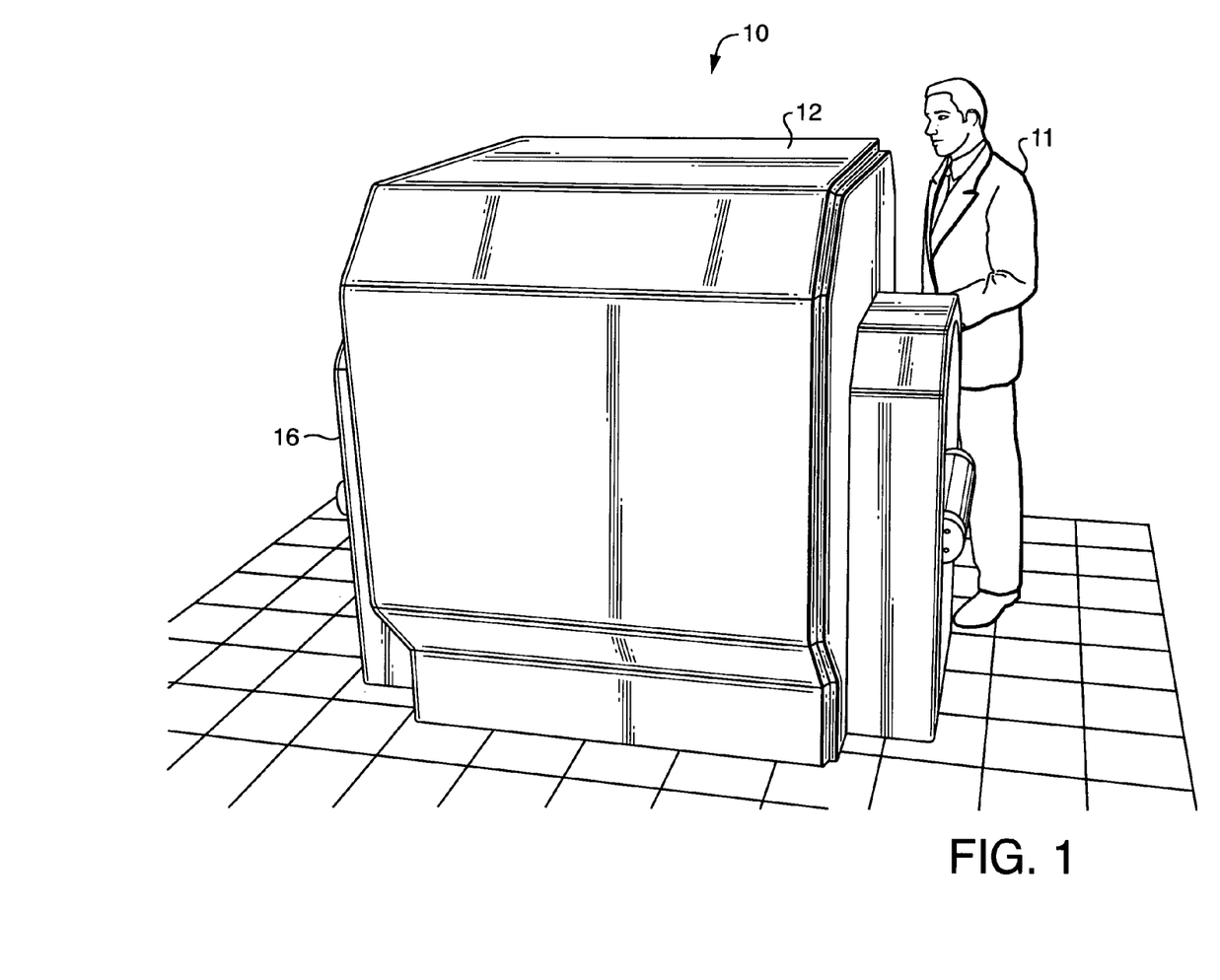
FIG. 1 is a side perspective view of an exemplary embodiment of an x-ray computed tomography scanning system constructed in accordance with the present disclosure and adapted to scan carry-on baggage for detection of explosives, drugs, and other contraband, and wherein a person is shown standing next to the system to provide a size comparison.
Figure 2:
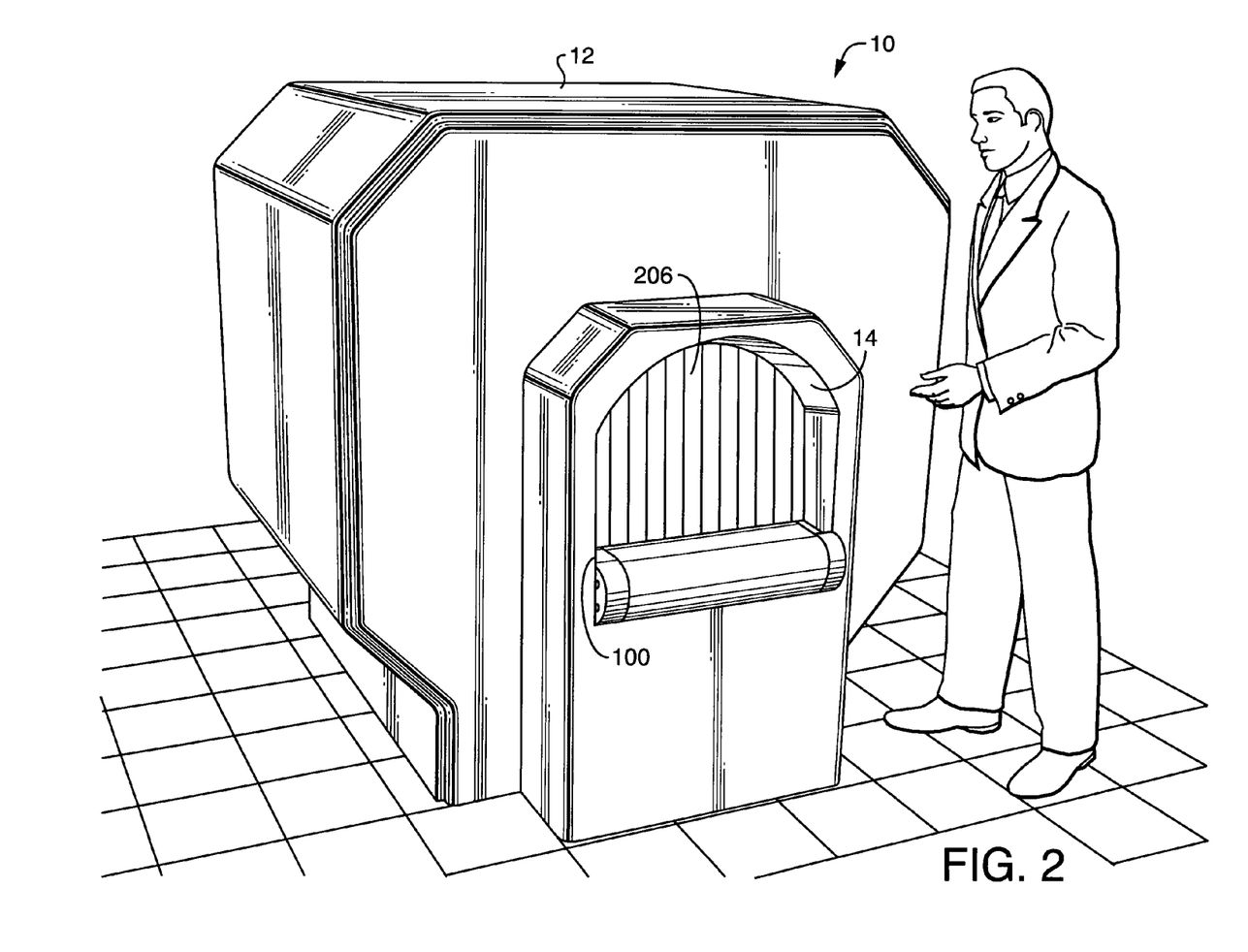
FIG. 2 is an end perspective view of the x-ray computed tomography scanning system and person of FIG. 1.

FIGS. 1 and 2 are perspective views of an exemplary embodiment of an x-ray computed tomography (CT) scanning system 10 constructed in accordance with the present disclosure and adapted to scan carry-on baggage for detection of explosives, drugs, and other contraband. In FIGS. 1 and 2, a person 11 is shown standing next to the system 10 to provide a size comparison.

The system 10 of the present disclosure generally scans for the same items and provides the same results as the EXACT™ AN6000 CT system, which is available from International Security Systems Corporation (www.analogic.com/ISS), which is a subsidiary of the assignee of the present disclosure, Analogic Corporation. The EXACT™ AN6000 CT system is covered by at least the following U.S. patents which are owned by Analogic Corporation: U.S. Pat. Nos. 5,661,774; 5,796,802; 5,818,897; 5,937,028; 6,185,272; 6,188,745; 6,256,404; 6,317,509 and 6,418,189, each of which is incorporated herein by reference.

Figure 3:
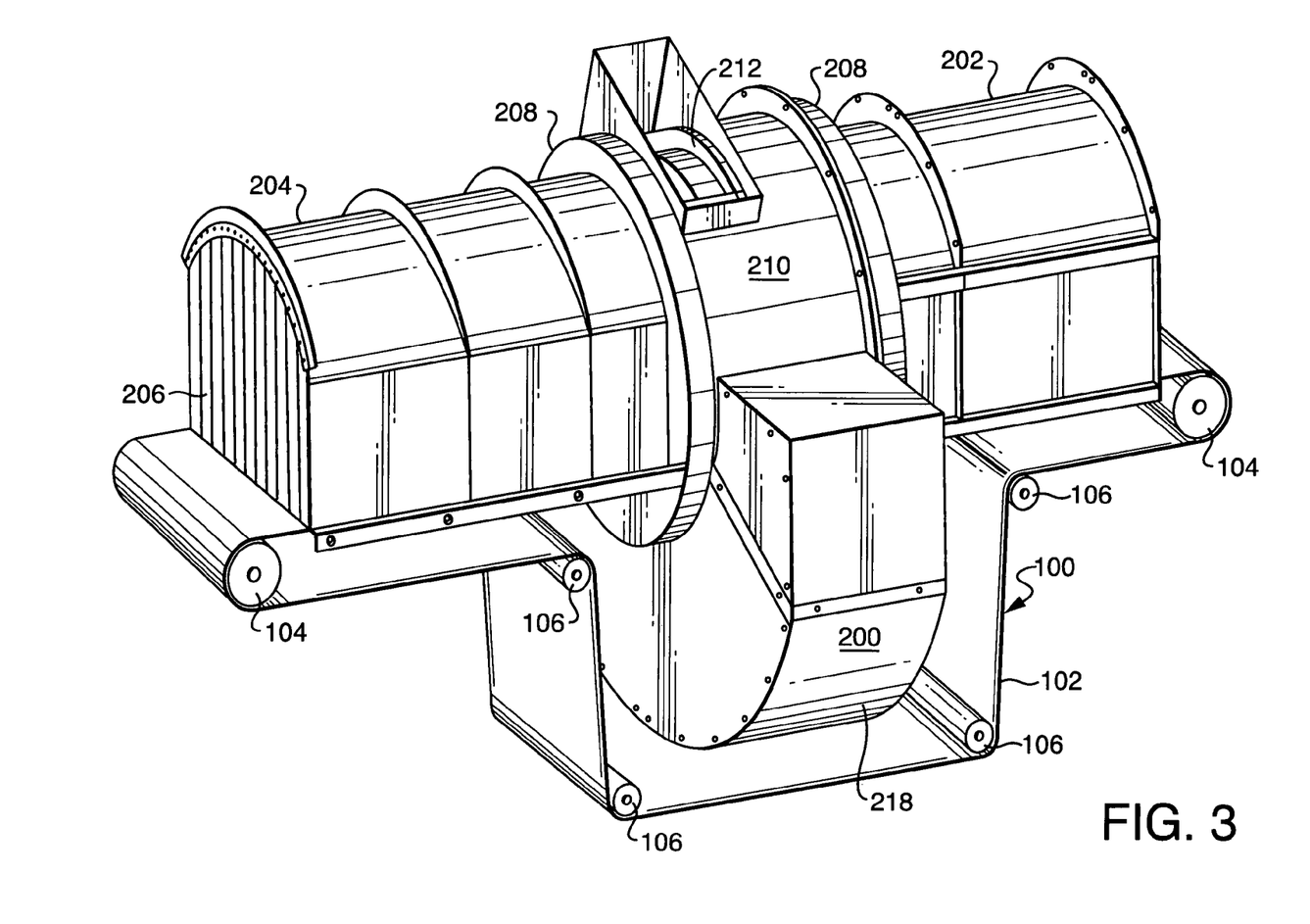
FIG. 3 is a side perspective view of the x-ray computed tomography scanning system of FIG. 1, shown with an outer housing and internal support structures removed to reveal an exemplary embodiment of conveyor system constructed in accordance with the present disclosure, and an exemplary embodiment of a rotating x-ray containment shield constructed in accordance with the present disclosure.
Figure 4:
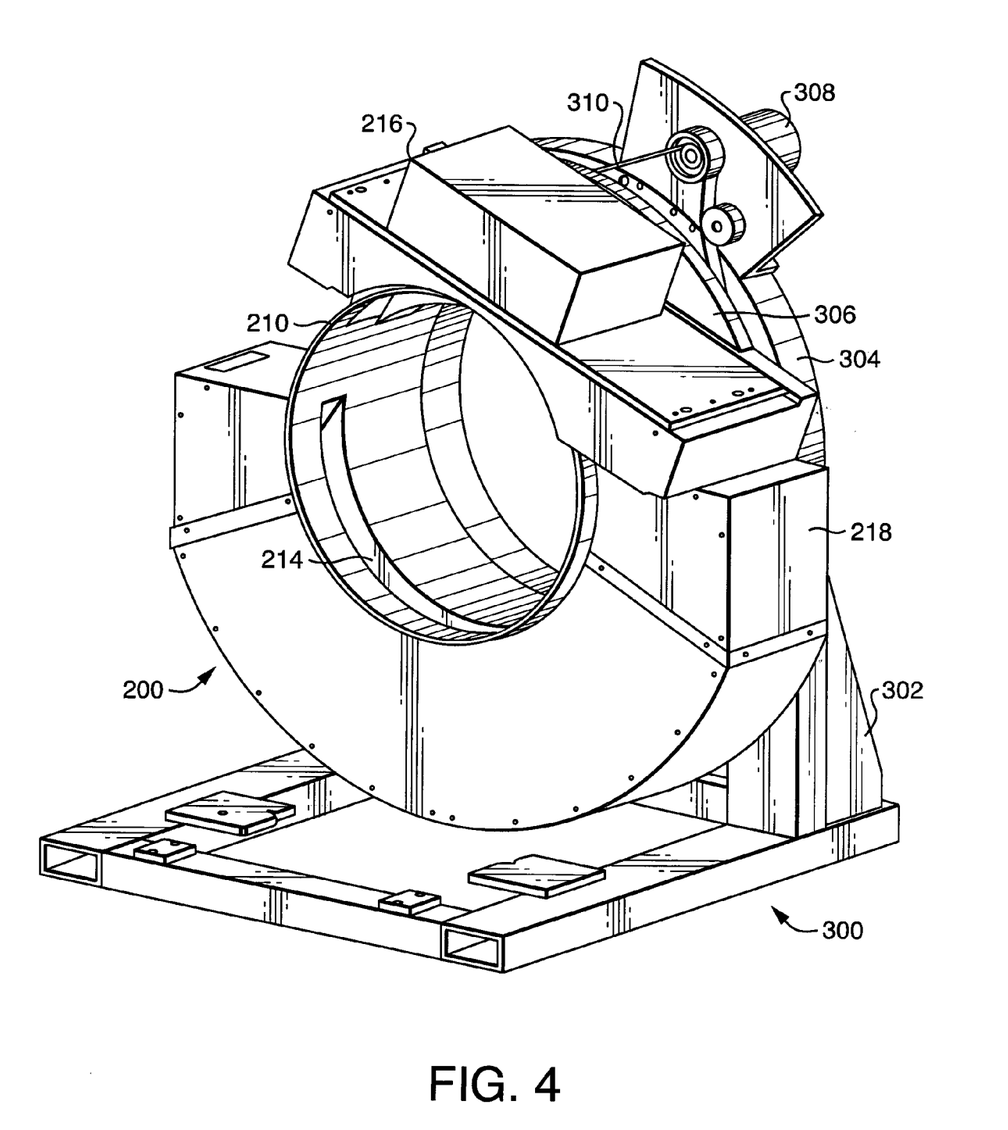
FIG. 4 is an end perspective view of a gantry of the x-ray computed tomography scanning system of FIG. 1, further showing the rotating x-ray shield of FIG. 3.
Figure 5:
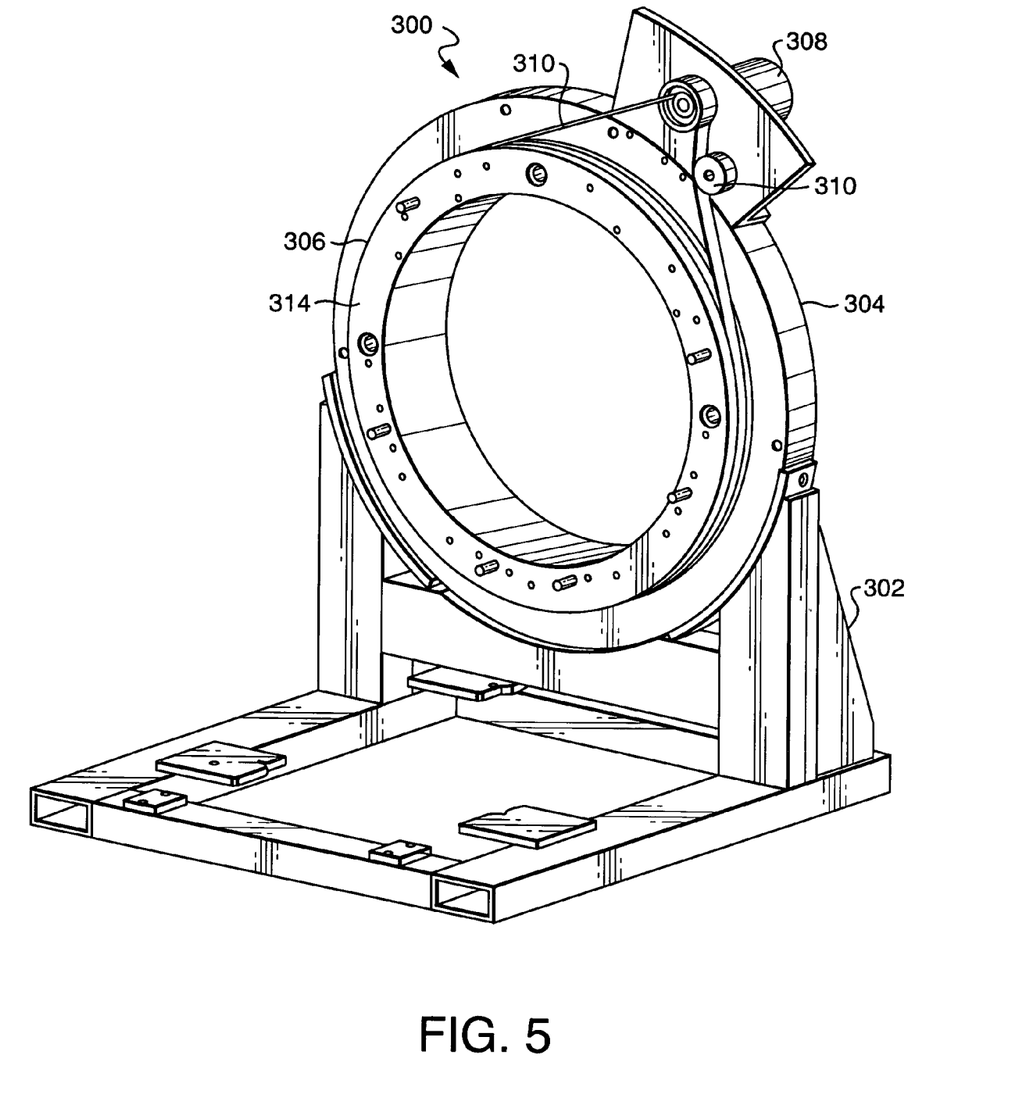
FIG. 5 is an end perspective view of the gantry of the x-ray computed tomography scanning system of FIG. 1, showing an exemplary embodiment of a rotatable inner race of the gantry.

The system 10 of the present disclosure, however, includes a new and improved conveyor system 100, as shown best in FIGS. 3 and 6–8, a new and improved rotating x-ray containment shield 200, as shown best in FIGS. 3 and 4, and a new and improved gantry support structure 300, as shown best in FIG. 5.

Like the EXACT™ AN6000, the system 10 of the present disclosure generates 3-D image data of all objects in a scanned piece of baggage, gathers all data in one pass, and allows automatic analysis of entire contents of the baggage. The system 10 includes an x-ray source and an x-ray detector (not shown). In one exemplary embodiment, the x-ray source is a dual energy, helical-cone-beam, multi-slice CT system that provides a complete set of CT images of an entire three-dimensional object as it is scanned, and the x-ray detector is a high efficiency, wide dynamic range, solid-state, two dimensional x-ray detector array.

Although not shown, the system 10 further includes a data acquisition system for receiving and processing signals generated by the detector array, and an x-ray tube control system for supplying power to, and otherwise controlling the operation of, the x-ray source. The x-ray tube control system can be, for example, a dual energy x-ray tube control system. The CT scanning system 10 is also preferably provided with a computer for processing the output of the data acquisition system and for generating the necessary signals for operating and controlling the system. The computer can include a CPU and a monitor, and may also include a processing center for respectively processing and displaying information including generated CT images in accordance with the teachings of the present disclosure.

In operation, the x-ray source generates from its focal spot a pyramidically shaped beam, often referred to as a "cone" beam x-ray that passes through a three dimensional imaging field, through which the carry-on baggage is positioned by the conveyor system. After passing through the scanned section of the baggage, the cone beam is received by the detector array, which in turn generates signals representative of physical attributes of portions of the baggage between the focal spot and the respective detector during the measuring interval. By way of example, one physical attribute can be the representative densities of portions of the baggage as determined as a function of the integral of the attenuation of the radiation beam passing through the container and any object therein. Where a dual energy power supply is utilized, the specific molecular weight of objects such as plastic explosives can be detected. Other physical attributes which may be detected will be evident to those skilled in the art. Thus, the scanning system 10 is not only useful for detecting plastic explosives, but the system can be used to detect other targeted objects, such as firearms and the like. A plurality of projections are generated at a corresponding plurality of projection angles with each 360° rotation of the gantry. In a well known manner, signals from the detector array can be initially acquired by a data acquisition system, and subsequently processed by a computer.

Referring first to FIGS. 1 and 2, the scanning system 10 includes an outer housing structure 12 having opposing openings 14, 16. The conveyor system 100 extends within the housing structure 12 between the opposing openings 14, 16 so that a piece of baggage placed on the conveyor system at one of the opening will be carried through the scanner system to the other of the openings.

Referring to FIG. 3, the system is shown with the outer housing structure 12 and internal support structures (e.g., legs and braces for supporting the conveyor system) removed. As shown the system includes the rotating x-ray containment shield 200, a first x-ray containment tunnel 202 extending to the rotating x-ray containment shield 200, and a second x-ray containment tunnel 204 extending from the rotating x-ray containment shield 200. The shield 200 and tunnels 204 are lined with a material absorbent of x-ray energy incident thereon during a tomographic scan, such as lead. Although not shown, open ends of the x-ray containment tunnels 202, 204 are positioned at the openings of the housing structure and include curtains 206 of x-ray absorbent material, such as lead. The conveyor system 100 passes through the tunnels 202, 204 and through the rotatable shield 200, as shown. The fixed tunnels 202, 204 are connected to the rotatable containment shield 200 through non-rotating fixed rings 208, which are made of, or lined with x-ray absorbent material, such as lead.

Still referring to FIG. 3, the rotating x-ray containment shield 200 includes an annular main body 210 extending between the fixed rings 208. The annular main body 210 is rotatable with respect to the fixed rings 208. Referring also to FIG. 4, the annular main body 210 defines an x-ray source aperture 212 diametrically opposed from an x-ray detector aperture 214. As shown best in FIG. 4, the x-ray containment shield 200 also includes an x-ray source housing 216 positioned over the x-ray source aperture 212 for supporting and containing an x-ray source (not shown), and an x-ray detector housing 218 positioned over the x-ray detector aperture 214 for supporting and containing an x-ray detector (not shown).

Components, including the x-ray source and the x-ray detector array, are mounted to the gantry and contained in the rotating x-ray containment shield 200. The shield prevents reflected x-ray beams from exiting the gantry area, while the curtains 206 prevent reflected beams from exiting the tunnels 202, 204, thereby protecting a nearby human from exposure to otherwise released energy. In a preferred embodiment, the shield 200 comprises sheet metal, for example sheet steel or stainless steel, lined with 2.5 mm thick lead sheeting.

As shown in FIG. 4, the x-ray containment shield 200 is supported for rotation on the gantry support structure 300. The present disclosure accordingly provides the shield 200 mounted to the gantry and rotatable therewith for absorbing randomly-directed x-rays. It is therefore unnecessary to line the entire surface of the system housing 12 with lead as in prior art systems. This configuration results in a shielding system 200 which is significantly reduced in weight and installation costs: the shield is designed to encompass only those areas where the active x-rays are required for system operation, shielding the remainder of the system 10 and the external environment from harmful radiation.

Referring to FIGS. 4 and 5, the gantry support structure 300 includes a stand 302 supporting an outer, non-rotating support ring 304, and an inner rotatable component ring 306 supported for rotation with respect to the support ring 304. A motor 308 is mounted on the support ring 304 and operatively connected to the component ring 306 through a pulley 310 received in an outer circumferential groove 312 of the component ring 306. Although not shown, the component ring 306 is rotatably supported on the support ring through a bearing system. U.S. Pat. Nos. 5,982,844, 6,188,743 and 6,337,894, which are owned by Analogic Corporation, provide examples of gantry bearing systems and gantry drive pulley systems which can be used with the gantry support structure 300 of the present disclosure, each of which is incorporated herein by reference.

As shown best in FIG. 5, the component ring 306 includes an annular mounting face 314 for receiving and supporting the x-ray containment shield and components including the x-ray source and the x-ray detector array. As shown, the mounting face 314 is provided with threaded bores and bolts for fastening the containment shield and components thereon.

Figure 6:
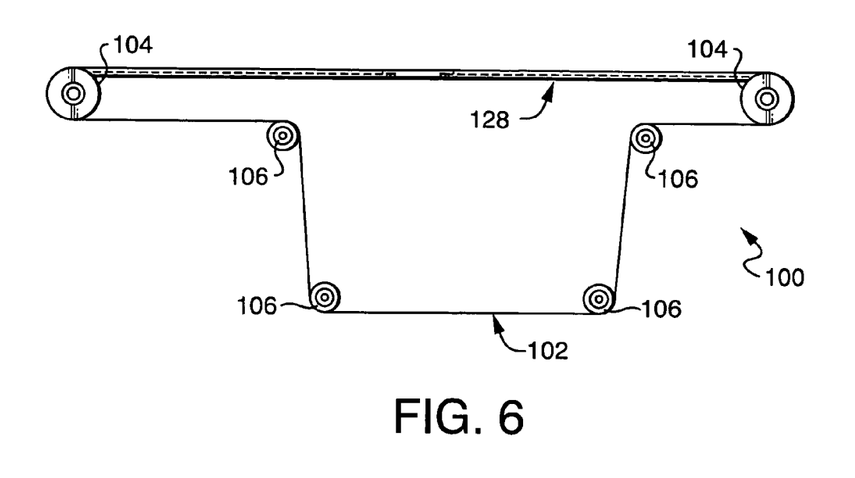
FIG. 6 is a side elevation view of the conveyor system of the x-ray computed tomography scanning system of FIG. 1.
Figure 7:
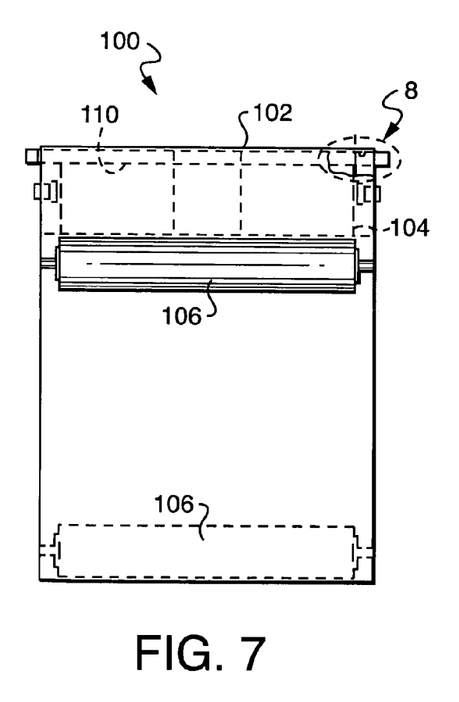
FIG. 7 is an end elevation view of the conveyor system of the x-ray computed tomography scanning system of FIG. 1.
Figure 8:
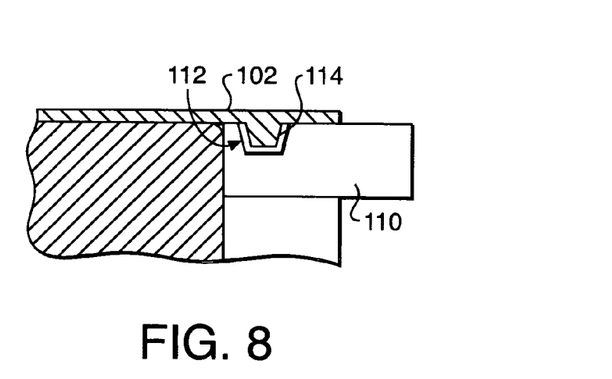
FIG. 8 is an enlarged sectional view of the conveyor system of the x-ray computed tomography scanning system of FIG. 1, contained in the circled portion "8" of FIG. 7.

Referring now to FIGS. 6–8, the conveyor system 100 includes a continuous conveyor belt 102 supported by two opposing pulleys 104 and four idler pulleys 106 (as shown best in FIG. 6). Although not shown, the scanning system 10 also includes at least one motor for rotating the drive pulleys 104 to move the conveyor belt 102. As shown best in FIG. 3, the conveyor belt 102 and the pulleys 104, 106 are positioned and arranged so that the conveyor belt 102 does not pass through, or bypasses, the x-ray scanning circle of the scanning system 10 on its return path. In other words, the conveyor belt 102 is directed around the x-ray containment shield 200 on it return path, and thus passes through the x-ray containment shield 200 only once when cycled around all the pulleys 104, 106. In this manner, the conveyor belt 102 does not receive as much x-rays during a scanning procedure.

The conveyor system 100 also includes skid plates 110 extending between the drive pulleys 104 and supporting the conveyor belt 102 as shown in FIGS. 6 and 7. As shown in FIGS. 7 and 8, the skid plates 110 are provided with grooves 112 which slidingly receive corresponding ridges 114 of the conveyor belt 102. The ridges 114 and the grooves 112 help maintain the conveyor belt 102 on the pulleys 104, 106 even when the direction of operation of the conveyor belt 102 is reversed. Alternatively, the skid plates 110 could include ridges received in grooves of the conveyor belt 102. In addition the pulleys 104, 106 could also include grooves or ridges for engagement with grooves or ridges of the conveyor belt 102.

It should be understood that the embodiments of the present disclosure described herein are merely exemplary and that a person skilled in the art may make variations and modifications to the embodiments described without departing from the spirit and scope of the present disclosures. Because certain changes may be made to the above-described appartus 10 without departing from the spirit and scope of the present disclosure, all matter contained in the above description or shown in the accompanying drawings shall be interpreted in an illustrative and not a limiting sense. All such equivalent variations and modifications are intended to be included within the scope of this disclosure as defined by the appended claims.

What is claimed is:

1. A tomography scanner system, comprising:
   a base;
   a gantry supported on the base and including,
      an outer, non-rotating support ring, and an inner rotatable component ring supported for rotation on the support ring about a rotation axis of the gantry;

an annular main body adapted for attachment to the inner rotatable component ring, the annular main body defining a source aperture and a detector aperture, wherein the source aperture is diametrically opposed on the annular main body from the detector aperture;

an x-ray source and an x-ray detector array secured to the annular main body for rotation with the annular main body;

an x-ray containment shield enclosing the x-ray source and the x-ray detector array and secured to the rotatable component ring for rotation with the component ring;

a first, non-rotating x-ray containment tunnel extending from an open end to the rotating x-ray containment shield coaxial with the rotation axis of the gantry, and a second, non-rotating x-ray containment tunnel extending from the rotating x-ray containment shield to an open end coaxial with the rotation axis of the gantry; and a continuous conveyor belt including a forward path extending through the tunnels and the gantry and a return path extending outside the tunnels and the gantry.

2. A tomography scanner system according to claim 1, wherein the component ring includes a mounting face extending perpendicular to the rotation axis and the x-ray source, the x-ray detector array and the x-ray containment shield are secured to the mounting face of the component ring.

3. A tomography scanner system according to claim 1, wherein a motor is mounted on the support ring and operatively connected to the component ring through a belt received in an outer circumferential groove of the component ring.

4. A tomography scanner system according to claim 1, wherein the x-ray source is a dual energy x-ray source.

5. A tomography scanner system according to claim 1, wherein the x-ray detector is a two dimensional x-ray detector array.

6. A tomography scanner system according to claim 1, further comprising a data acquisition system for receiving and processing signals generated by the detector array, and an x-ray tube control system for supplying power to, and controlling the operation of, the x-ray source.

7. A tomography scanner system according to claim 6, further comprising a computer for processing the output of the data acquisition system and for generating the necessary signals for operating and controlling the system.

8. A tomography scanner system according to claim 1, wherein the rotating x-ray containment shield is lined with a material absorbent of x-ray energy incident.

9. A tomography scanner system according to claim 8, wherein the material absorbent of x-ray energy incident comprises lead.

10. A tomography scanner system according to claim 1, wherein the tunnels are lined with a material absorbent of x-ray energy incident.

11. A tomography scanner system according to claim 10, wherein the material absorbent of x-ray energy incident comprises lead.

12. A tomography scanner system according to claim 1, wherein the open ends of the x-ray containment tunnels include curtains of x-ray absorbent material.

13. A tomography scanner system according to claim 1, wherein the non-rotating x-ray containment tunnels are connected to the rotatable x-ray containment shield through non-rotating fixed rings, wherein the x-ray containment shield is rotatable with respect to the fixed rings.

14. A tomography scanner system according to claim 13, wherein the non-rotating fixed rings include x-ray absorbent material.

15. A tomography scanner system according to claim 1, further comprising an x-ray source housing positioned over the x-ray source aperture and supporting and containing the x-ray source, and an x-ray detector housing positioned over the x-ray detector aperture and supporting and containing the x-ray detector.

16. A tomography scanner system according to claim 1, wherein the rotating x-ray containment shield comprises sheet metal lined with lead sheeting.

17. A tomography scanner system according to claim 1, wherein the continuous conveyor belt is supported by pulleys and at least one motor for rotating the pulleys to move the conveyor belt.

18. A tomography scanner system according to claim 17, further comprising skid plates extending between the pulleys and supporting the conveyor belt.

19. A tomography scanner system according to claim 18, wherein the skid plates include grooves which slidingly receive ridges of the conveyor belt.

20. A tomography scanner system according to claim 18, wherein the skid plates include ridges slidingly received in grooves of the conveyor belt.

21. A tomography scanner system according to claim 17, wherein the pulleys include grooves which receive ridges of the conveyor belt.

* * * * *